(12) United States Patent
Yuan et al.

(10) Patent No.: US 12,281,414 B2
(45) Date of Patent: Apr. 22, 2025

(54) ELECTROSPINNING COLLECTOR FOR THE PRODUCTION OF THREE-DIMENSIONAL ELECTROSPUN CONSTRUCTS

(71) Applicant: Naval Medical Research Center, Silver Spring, MD (US)

(72) Inventors: Tony T Yuan, Boerne, TX (US); Kirstin Jones, Sugar Land, TX (US); Cortes Williams, Sugar Land, TX (US)

(73) Assignee: The United States of America, as Represented by the Secretary of the Navy, Silver Spring, MD (US)

( * ) Notice: Subject to any disclaimer, the term of this patent is extended or adjusted under 35 U.S.C. 154(b) by 0 days.

(21) Appl. No.: 17/848,288

(22) Filed: Jun. 23, 2022

(65) Prior Publication Data
US 2023/0002935 A1    Jan. 5, 2023

Related U.S. Application Data
(60) Provisional application No. 63/214,486, filed on Jun. 24, 2021.

(51) Int. Cl.
| | |
|---|---|
| *B29C 33/38* | (2006.01) |
| *A61L 27/24* | (2006.01) |
| *B29C 33/40* | (2006.01) |
| *B29C 33/42* | (2006.01) |
| *D01D 5/00* | (2006.01) |
| *B82Y 5/00* | (2011.01) |
| *B82Y 40/00* | (2011.01) |

(52) U.S. Cl.
CPC ............ *D01D 5/0076* (2013.01); *A61L 27/24* (2013.01); *D01D 5/0023* (2013.01); *A61L 2400/12* (2013.01); *B82Y 5/00* (2013.01); *B82Y 40/00* (2013.01)

(58) Field of Classification Search
CPC ......... B29C 33/38; B29C 33/40; B29C 33/42; D01D 5/0076
USPC .................................. 425/174.8 E, 377, 470
See application file for complete search history.

(56) References Cited

U.S. PATENT DOCUMENTS
2011/0250308 A1* 10/2011 Jun ...................... D01D 5/0076
425/174.8 E

OTHER PUBLICATIONS
Angammana, C.J. and S.H. Jayaram. A theoretical understanding of the physical mechanisms of electrospinning. in Proc. ESA Annual Meeting on Electrostatics. 2011.
Kai, D., S.S. Liow, and X.J. Loh, Biodegradable polymers for electrospinning: towards biomedical applications. Materials Science and Engineering: C, 2014. 45: p. 659-670.
Tohman, M.M., et al., Electrospinning and electrically forced jets. I. Stability theory. Physics of fluids, 2001. 13(8): p. 2201-2220.
Vaseashta, A., Controlled formation of multiple Taylor cones in electrospinning process. Applied Physics Letters, 2007. 90(9): p. 093115.

(Continued)

*Primary Examiner* — Leo B Tentoni
(74) *Attorney, Agent, or Firm* — Ning Yang

(57) ABSTRACT

An electrospinning apparatus and method for producing three-dimensional electrospun constructs is disclosed. Further, electrospinning apparatus and method 3D electrospun collagen based mineralized nanofibrous scaffold for alveolar ridge preservation prior to dental implant therapy are disclosed.

10 Claims, 15 Drawing Sheets

(56) References Cited

OTHER PUBLICATIONS

Kong, C.S., et al., Electrospinning mechanism for producing nanoscale polymer fibers. Journal of Macromolecular Science®, Part B: Physics, 2010. 49(1): p. 122-131.
Doshi, J. and D.H. Reneker. Electrospinning process and applications of electrospun fibers. in Conference Record of the 1993 IEEE Industry Applications Conference Twenty-Eighth IAS Annual Meeting. 1993. IEEE.
Deitzel, J.M., et al., Controlled deposition of electrospun poly (ethylene oxide) fibers. Polymer, 2001. 42(19): p. 8163-8170.
Shabani, I., et al., Cellular infiltration on nanofibrous scaffolds using a modified electrospinning technique. Biochemical and biophysical research communications, 2012. 423(1): p. 50-54.
Ghasemi-Mobarakeh, L., et al., The thickness of electrospun poly (ε-caprolactone) nanofibrous scaffolds influences cell proliferation. The International journal of artificial organs, 2009. 32(3): p. 150-158.
Lowery, J.L., N. Datta, and G.C. Rutledge, Effect of fiber diameter, pore size and seeding method on growth of human dermal fibroblasts in electrospun poly (ε-caprolactone) fibrous mats. Biomaterials, 2010. 31(3): p. 491-504.
Haider, A., S. Haider, and I.-K. Kang, A comprehensive review summarizing the effect of electrospinning parameters and potential applications of nanofibers in biomedical and biotechnology. Arabian Journal of Chemistry, 2018. 11(8): p. 1165-1188.
Rnjak-Kovacina, J. and A.S. Weiss, Increasing the pore size of electrospun scaffolds. Tissue Engineering Part B: Reviews, 2011. 17(5): p. 365-372.
Nam, J., et al., Improved cellular infiltration in electrospun fiber via engineered porosity. Tissue engineering, 2007. 13 (9): p. 2249-2257.
Ji, C., et al., Fabrication of poly-DL-lactide/polyethylene glycol scaffolds using the gas foaming technique. Acta biomaterialia, 2012. 8(2): p. 570-578.
Jun, I., et al., Electrospun fibrous scaffolds for tissue engineering: Viewpoints on architecture and fabrication. International journal of molecular sciences, 2018. 19(3): p. 745.
Bulysheva, A.A., et al., Low-temperature electrospun silk scaffold for in vitro mucosal modeling. Journal of Biomedical Materials Research Part A, 2012. 100(3): p. 757-767.
Yang, X., J.D. Shah, and H. Wang, Nanofiber enabled layer-by-layer approach toward three-dimensional tissue formation. Tissue Engineering Part A, 2009. 15(4): p. 945-956.
Blakeney, B.A., et al., Cell infiltration and growth in a low density, uncompressed three-dimensional electrospun nanofibrous scaffold. Biomaterials, 2011. 32(6): p. 1583-1590.
Kim, M.S., et al., Highly porous 3D nanofibrous scaffolds processed with an electrospinning/laser process. Current Applied Physics, 2014. 14(1): p. 1-7.
Mondal, D., M. Griffith, and S.S. Venkatraman, Polycaprolactone-based biomaterials for tissue engineering and drug delivery: Current scenario and challenges. International Journal of Polymeric Materials and Polymeric Biomaterials, 2016. 65(5): p. 255-265.
Tomlin, E.M., S.J. Nelson, and J.A. Rossmann, Ridge preservation for implant therapy: a review of the literature. The open dentistry journal, 2014. 8(1).
Barone, A., et al., Xenograft versus extraction alone for ridge preservation after tooth removal: a clinical and histomorphometric study. Journal of periodontology, 2008. 79(8): p. 1370-1377.
Horowitz, R., D. Holtzclaw, and P.S. Rosen, A review on alveolar ridge preservation following tooth extraction. Journal of Evidence Based Dental Practice, 2012. 12(3): p. 149-160.
Scabbia, A. and L. Trombelli, A comparative study on the use of a HA/collagen/chondroitin sulphate biomaterial (Biostite®) and a bovine-derived HA xenograft (Bio-Oss®) in the treatment of deep intra-osseous defects. Journal of clinical periodontology, 2004. 31(5): p. 348-355.
Marinucci, L., et al., Effects of hydroxyapatite and Biostite® on osteogenic induction of hMSC. Annals of biomedical engineering, 2010. 38(3): p. 640-648.
Zhu, Y., et al., Surface modification of polycaprolactone membrane via aminolysis and biomacromolecule immobilization for promoting cytocompatibility of human endothelial cells. Biomacromolecules, 2002. 3(6): p. 1312-1319.
Kokubo, T. and H. Takadama, How useful is SBF in predicting in vivo bone bioactivity? Biomaterials, 2006. 27(15): p. 2907-2915.
Drew, C., et al., The effect of viscosity and filler on electrospun fiber morphology. Journal of Macromolecular Science, Part A, 2003. 40(12): p. 1415-1422.
Nezarati, R.M., M.B. Eifert, and E. Cosgriff-Hernandez, Effects of humidity and solution viscosity on electrospun fiber morphology. Tissue Engineering Part C: Methods, 2013. 19(10): p. 810-819.
Yang Y., Jia Z., Liu J., Li Q., Hou L., Wang L., and Guan Z. Effect of electric field distribution uniformity on electrospinning. Journal of Applied Physics 103, 104307 (2008).

\* cited by examiner

| Material | Geometric Volume (mm³) | Pycnometry Volume (mm³) | Pycnometry Porosity (%) |
|---|---|---|---|
| Copper Mesh | 30.87 | 4.1 | 86.71849692 |
| Variable Ground | 36.65 | 7 | 80.90040928 |
| Probes | 23.13 | 4 | 82.70644185 |
| Flat Plate | 1.8 | 0.7 | 61.11111111 |

* Change in peak indicates phosphate group
^ Indicates OH group found in hydroxyapatite
! Amide peak indicative of collagen

ELECTROSPINNING COLLECTOR FOR THE PRODUCTION OF THREE-DIMENSIONAL ELECTROSPUN CONSTRUCTS

CROSS-REFERENCE TO RELATED APPLICATION

This application claims priority to U.S. Provisional Application No. 63/214,486, filed on Jun. 24, 2021, which is hereby incorporated by reference.

FEDERALLY SPONSORED RESEARCH AND DEVELOPMENT

This invention was made with government support under Contract #N6264521F0088 awarded by Department of the Navy. The government has certain rights in the invention.

FIELD OF THE INVENTION

This invention related to an apparatus and a method for the manufacture of a three-dimensional electrospun construct, and the respective use of this method and apparatus for the preparation of collagen based mineralized nanofibrous scaffold.

BACKGROUND

Electrospinning is a technique used to produce nanofibers from many different types of polymers [1, 2] by applying a high voltage to a polymer solution, which helps drive fiber formation towards a grounded collector. While the setup and process is fairly easy, the theoretical understanding of electrospinning is complicated, and is dependent on the interaction of many forces, such as surface tension of the polymer solution and the electrical forces acting on the polymer solution [3]. When voltage is applied to the polymer solution, it becomes charged and begins to stretch towards the grounded collector. As electrical charge increases, the polymer solution that has collected on the tip of the spinneret elongates to form what is known as a Taylor cone [4]. A critical value is met when the electric force is greater than the surface tension of the polymer solution. At this point the polymer solution is ejected from the Taylor cone [5]. As the solution travels towards the collector, solvent evaporates, and fibers continuously collect to form the scaffold [6]. Electrospun fibers retain much of their charge once they are deposited onto the grounded collector [7]. Because of this, as well as the rate of evaporation of the solvent system [8], they are pulled toward the grounded collector as they deposit, which compresses the fiber layers on top of each other and produces a scaffold that is a thin sheet. There is evidence suggest that electrospun fibers maintain static charge during the electrospinning process, which could be used to manipulate the fibers into three-dimensional constructs by altering the electrical field around the deposited fibers [7]. However, this form of electrospinning manipulation has not been extensively investigated.

Due to its low cost, ease of use, and high compatibility with a large diversity of polymers, electrospinning has recently become a popular method of creating scaffolds for biomaterial applications. Traditionally, electrospinning is performed using a plate collector that produces flat, sometimes referred to as two-dimensional or 2D, scaffolds with dense and tightly packed fibers. While successful in some applications, such as drug delivery and wound dressings, this method of electrospinning produces only "paper-thin" scaffolds that limit cellular infiltration [9]. Specifically, as seen when spun with polycaprolactone (PCL), scaffold thicknesses range between 0.1 mm and 0.6 mm based on electrospinning time [9]. The application of these thin densely packed scaffolds is largely restricted to areas that do not require volumetric fill. Additionally, pore size and porosity have also been shown to affect cellular response [10, 11], and compacted scaffold limit tissue growth. Thus, there is the critical need for a scaffold that is less densely packed, which offers improved scaffold characteristics and featuring desirable three-dimensional (3D) architecture. A 3D scaffold would not only promote improved cellular infiltration, but also advance the applications in which electrospinning can be utilized. [11]. These features are especially important when using the electrospun scaffolds to hold a volume as needed in many biomedical regenerative applications. The 3D architecture is especially important when the electrospun scaffolds is used in many biomedical regenerative applications to hold a volume.

Modifications to the electrospinning parameters have been extensively studied. Most of the studies concentrate on increasing pore size and porosity of electrospun scaffolds. Researchers experimented with increasing fiber diameter, using a rotating mandrel collector, wet electrospinning, and sacrificial material electrospinning [12]. While some of these studies failed to report on scaffolds' pore size, others utilized flat plate electrospinning. Other methods of increasing pore size include salt leaching, gas foaming, and cryogenic electrospinning, however, these methods were investigated using flat plate spun scaffolds [12]. Salt leaching involves the dissolution of salt in the electrospinning solution. Once a scaffold has been produced, the fibers are exposed to water and the salt is leached out of the scaffold leaving large pores throughout [13]. Gas foaming involves the introduction of inert gas into a polymer solution to introduce bubbles in the material that pushes the scaffold apart, creating pores. While, these pores are appropriate in size for cellular infiltration, there is generally no interconnectivity of these pores and the architecture does not mimic that of the extracellular matrix (ECM) [14]. Cryogenic electrospinning uses ice crystal formation during the electrospinning process that are removed during post-processing of scaffolds by freeze-drying, leaving large pores within the scaffolds. Although this method does create void spaces that promote cellular infiltration, the cryogenic electrospinning method does not provide easily controlled pore size due to the random nucleation of water crystals and have not been tested in generation of 3D constructs [15, 16].

The development of 3D scaffolds has been investigated previously, reported in the literature through the development of new collector types, and post-fabrication scaffold manipulation. A previous study looked to create a 3D scaffold by layering multiple scaffolds [17]. However, this technique does not support a uniform morphology or address the issue of improving pore size and porosity. Another method of creating 3D scaffolds is the development of a different type of collector, capable of spinning 3D constructs using what is known as focused, low density, uncompressed nanofiber (FLUF) electrospinning [18]. However, the resulting constructs are not always reproducible. Others explored the use of a femtosecond laser burning pores into electrospun scaffolds [19]. However, the resulting structure does not mimic the extracellular matrix (ECM). The use of focusing halogen lights on a specific area during electrospinning has also been reported as a way to produce volumetric scaffolds [8]. However, no comparisons were made on porosity, and there was no statistical increase in the pore size of the volumetric scaffolds. While current research efforts have tried to address the production of 3D scaffolds, there still exists a need for an easily reproducible method of producing 3D electrospun constructs that do not require post-processing or altering the naturally electrospun construct.

DETAILED DESCRIPTION OF THE DRAWINGS

Figure 7:
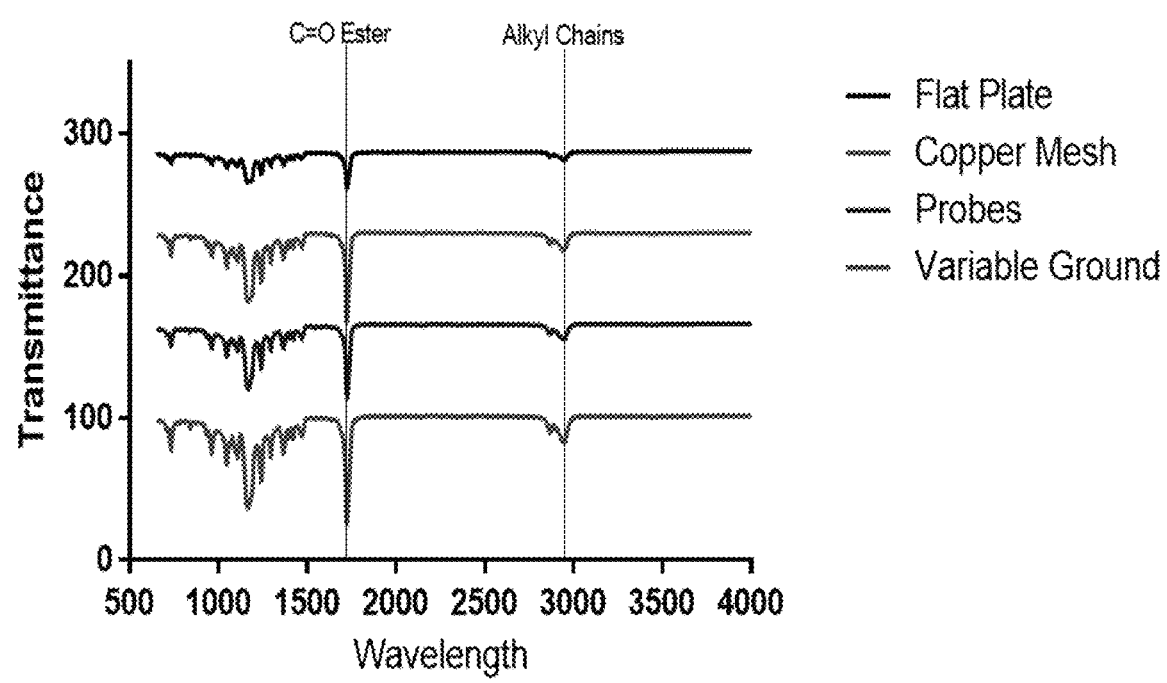

FIG. 7 FTIR of scaffolds spun on each collector type show that the collector used does not affect chemical composition of the polymer.

Figure 8:
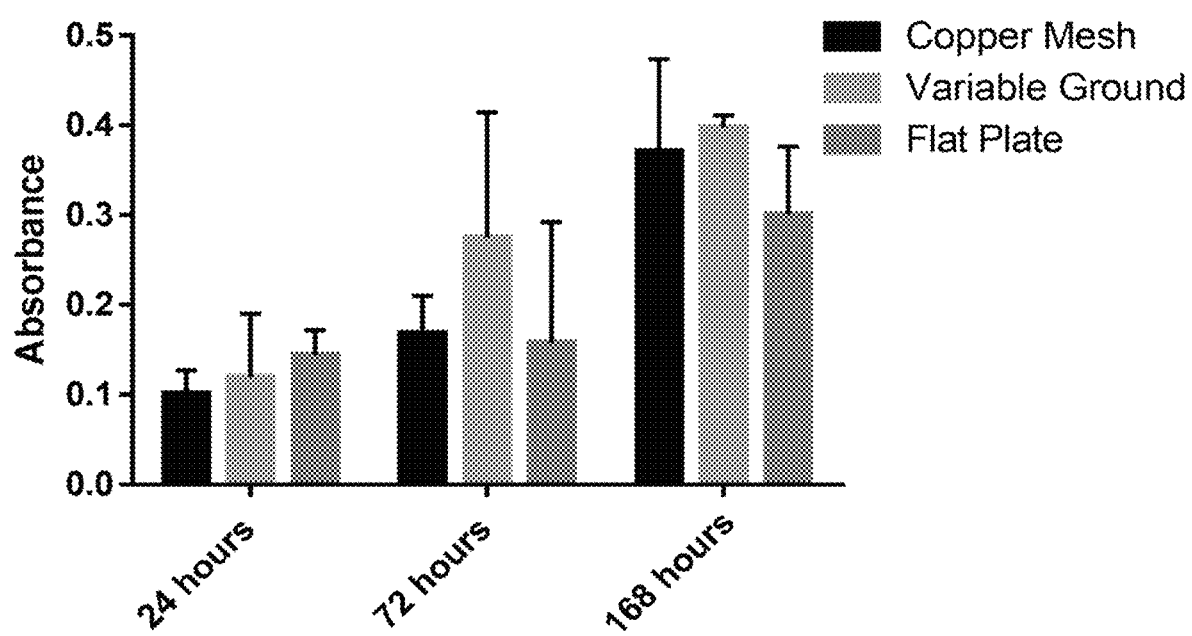

FIG. 8 Viability of Saos-2 osteosarcomas on the surfaces of scaffolds spun from different collectors.

Figure 9:
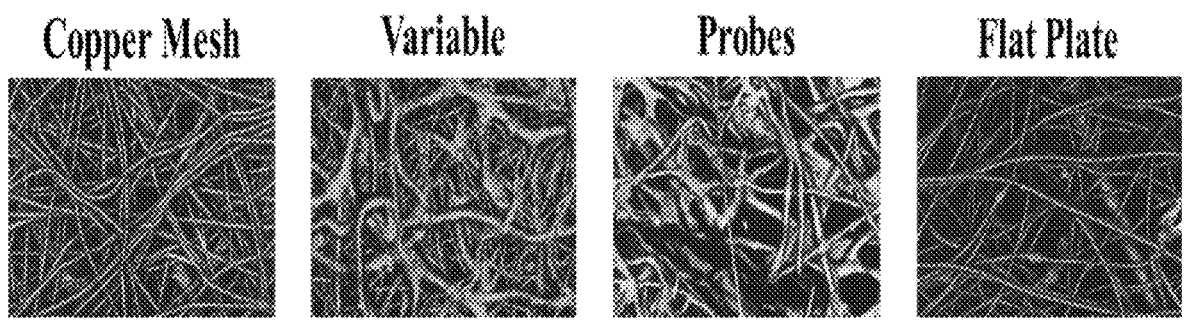

FIG. 9 shows scaffolds produced using each collector, observed using laser microscopy.

Figure 10:
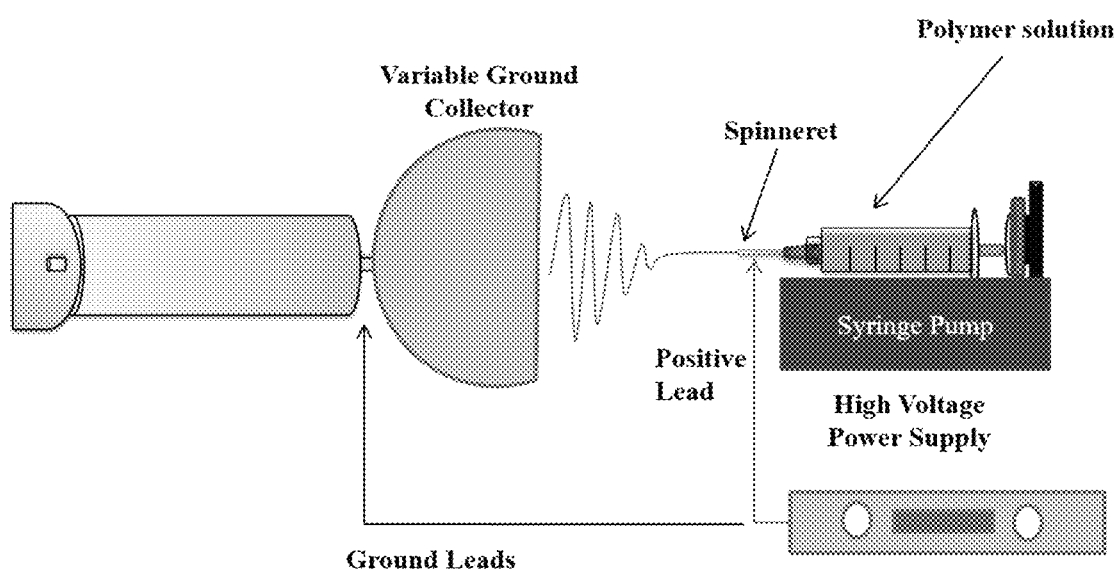

FIG. 10 shows the general set up of an electrospinning apparatus using the inventive 3D collector.

Figure 11:
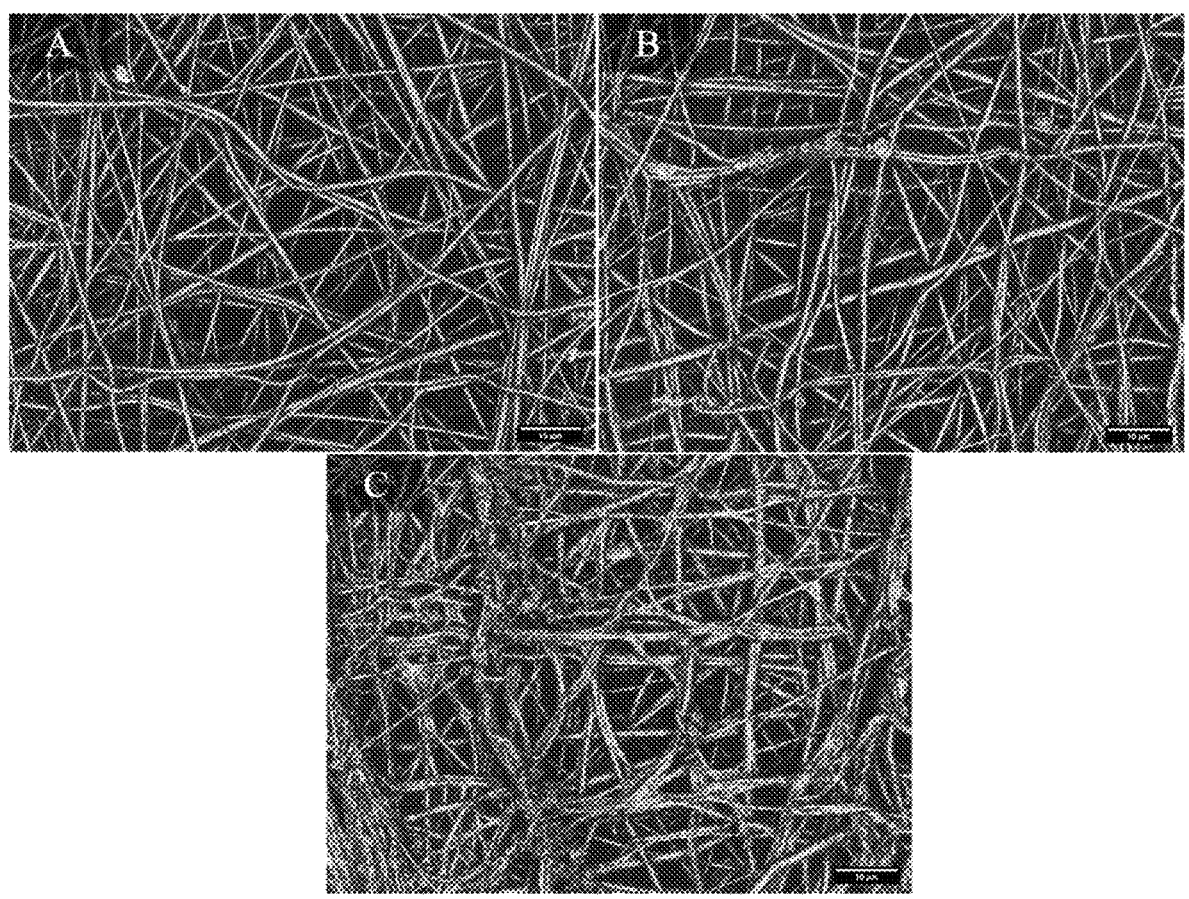

FIG. 11 shows laser microscopy images taken at 150× magnification of collagen attached scaffold (A), collagen attached scaffold mineralized for 5 days (B), and collagen scaffold mineralized for 7 days (C).

Figure 12:
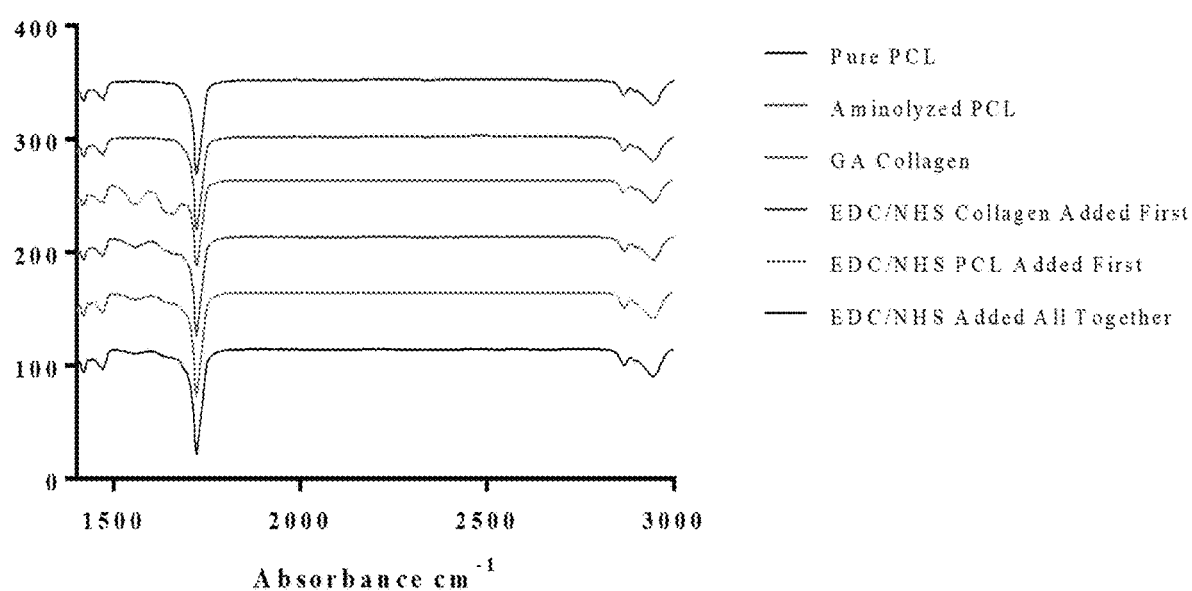

FIG. 12 shows FTIR comparison of different techniques used to attach collagen to the surface of PCL.

Figure 13:
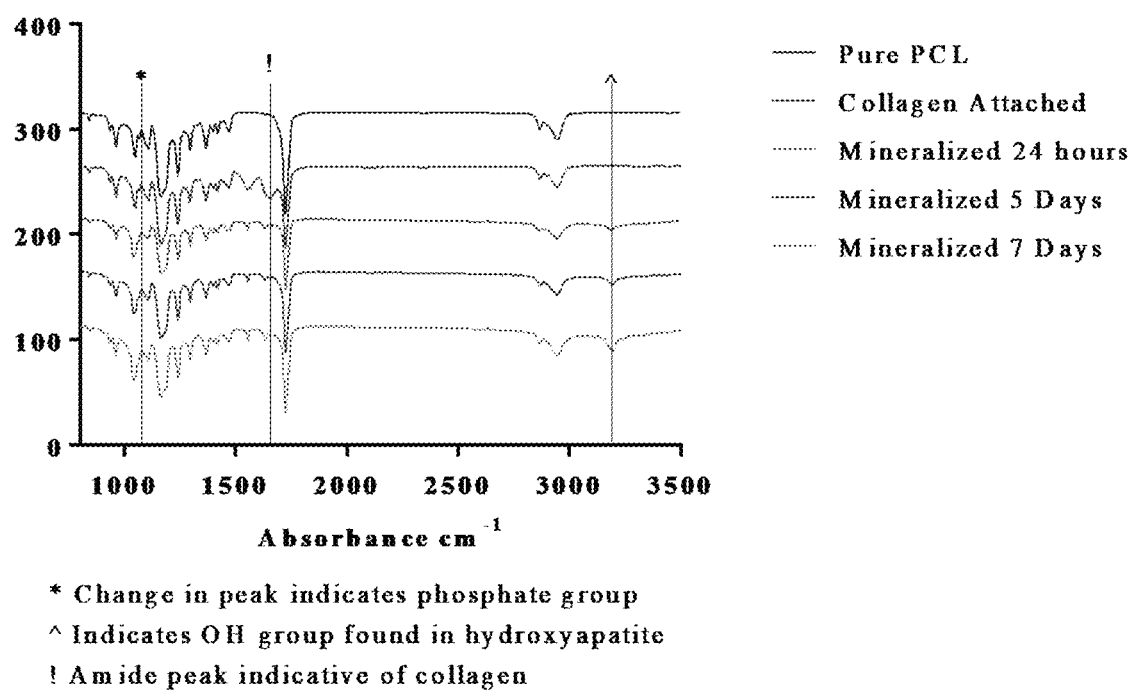

FIG. 13 shows FTIR comparison of scaffolds mineralized for 1, 5, or 7 days.

Figure 14:
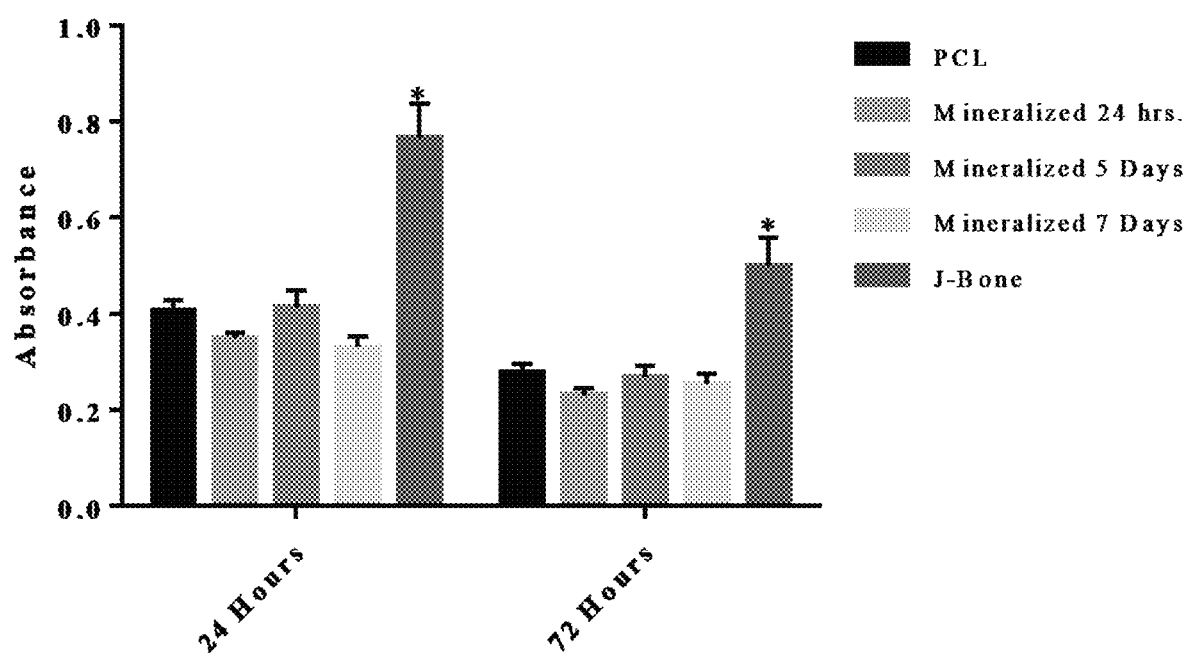

FIG. 14 shows CCK8 cell viability with osteoblasts seeded on mineralized scaffolds (n=4) for up to 72 hours. *Indicates a statistically significant difference between J-Bone and all other scaffolds. Significance was established at $p<0.05$.

DETAILED DESCRIPTION OF THE INVENTION

Figure 1A:
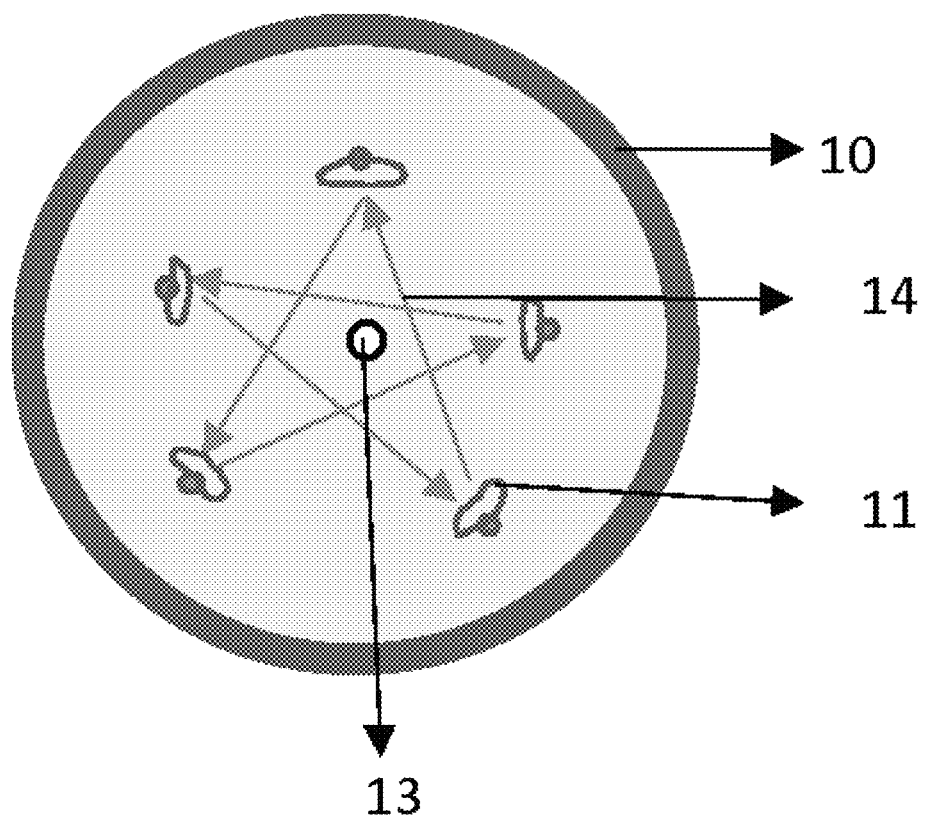
FIG. 1A shows the top view of an enablement of the variable ground collector, which promotes collection of electrospun fibers in a star pattern.
Figure 1B:
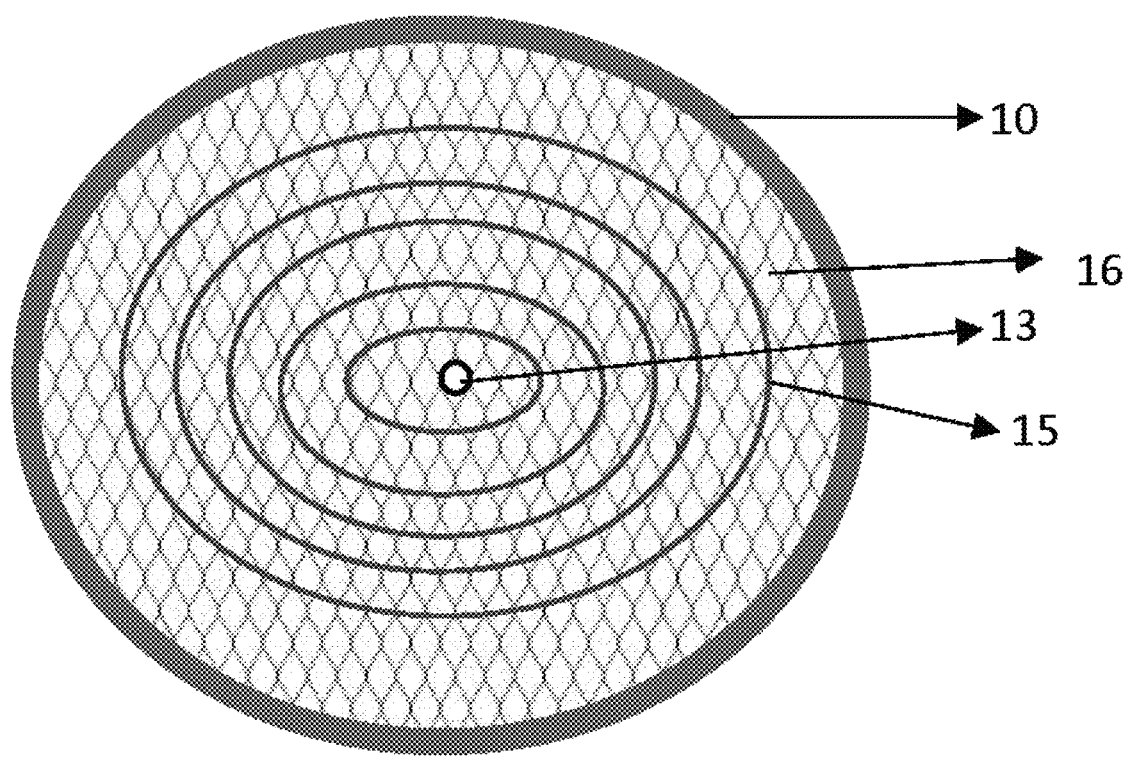
FIG. 1B shows the top view of an enablement of the variable ground mesh collector, which promotes even distribution of fibers across a copper grid.

I. Design Concept of an Improved Collector Capable of Producing 3D Electrospun Constructs This invention is directed to an electrospinning collector that is capable of producing 3-dimensional (3-D) constructs or scaffolds with minimal post-processing, which does not alter the existing architecture of the construct or scaffold. Two novel 3D electrospinning collector are designed to accomplish this task. The first design is shown in FIG. 1A, involves utilizing a collector (10) that promotes the distribution of an electrical grounded force that neither aggregates in one area of the collector nor across the entirety of the collector. Instead, the electrical ground rotates between probes embedded inside a hollow non-conducting collector (11) forming unique pattern (14) as the collector rotates. It is proposed that if the electrospun fibers are being pulled in opposing directions during electrospinning, the fibers would have less time to compress onto each other, thus promoting a 3D construct with improving porosity and pore size. The second design is shown in FIG. 1B, involves an electrical ground that is evenly distributed across a copper gridded mesh (16) covering a hollow non-conducting collector (10). The theory behind this design is that even ground of the collector will promote even distribution of fibers (15) across the collector. The gridded design will allow higher porosity and pore size in between grids because there is no solid platform for the fibers to compress on. As such, they will be collecting in open space.

II. Basic Design of Inventive Three-Dimensional Electrospinning Collectors

Figure 3:
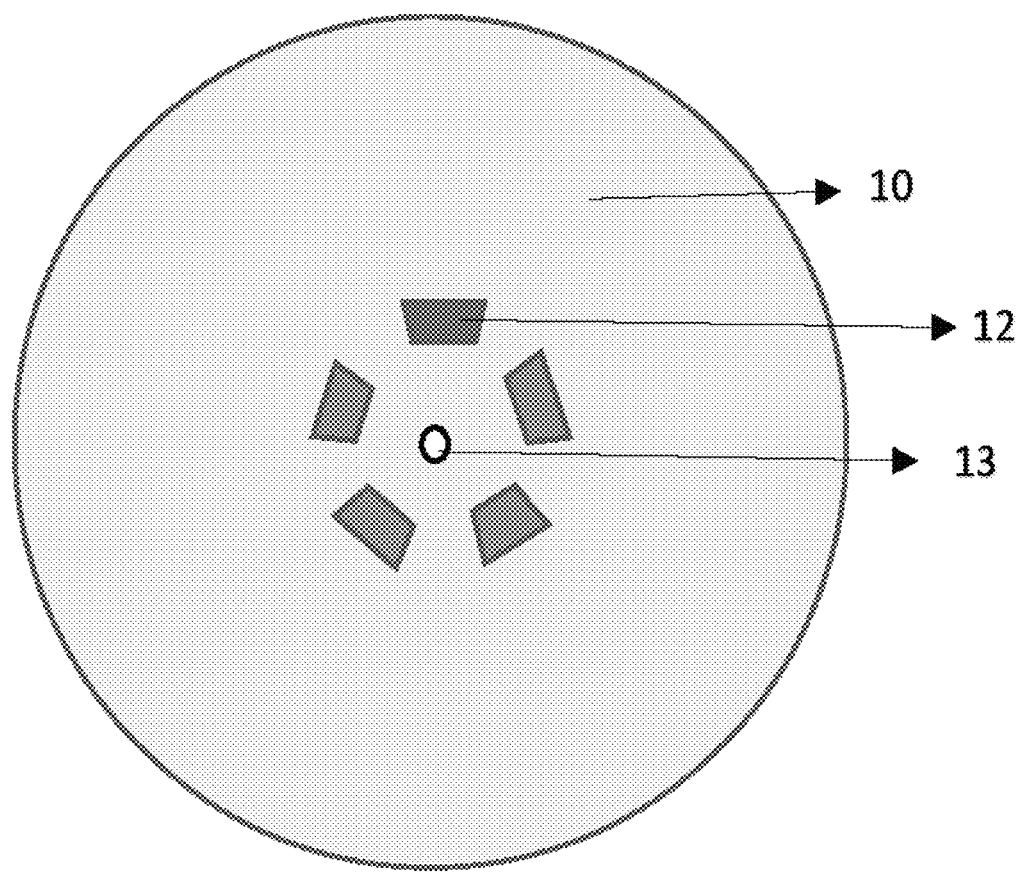
FIG. 3 shows a bottom view of the prototype variable ground collector, wherein each copper probe was electrically grounded independently from each another.

In one embodiment of the present invention, the three-dimensional electrospinning collector, comprising: a hollow non-conductive collector body (10); a plurality of grounding probes (11) that are embedded inside the collector body (10) approximately halfway down the sphere in equidistant directions, and each grounding probe is electrically grounded independently from one another (FIG. 3). The hollow collector body may be take many shape such as semi-sphere, semi-football, rectangular, or cube etc. The collector body may be made of any solid or semi solid electrical non-conductive materials, including but not limited to Styrofoam, polycaprolactone (PCL), poly(l-lactic acid) (PLA), poly(l-lactic-co-glycolicacid) (PLGA), acrylonitrile butadiene styrene (ABS), and nylon. Based on the materials used, the collector body (10) may be form using a variety of manufacturing techniques, including but not limiting to machine cutting, extrusion, 3D printing etc. The size of the collector is selected based on the size of the 3D construct that it aim to collect. The hollow non-conductive collector body may further comprises a means for attaching to a rotating mandrel. In one embodiment, the collector holds onto the rotating mandrel via a hole (13) in the center of the collector, which is slightly smaller than the mandrel. Other commonly used affixation methods may also be used as long as it does not alter the electrical non-conducting property of the collector body. A plurality of grounding probes are evenly embedded inside the collector body. In one embodiment, the grounding probes are embedded approximately halfway down inside the hollow semi-sphere collector body in equidistant directions. The number of the ground probe (11) or the direction of the probe (11) are determined based by the desired electrical field distribution, and are depended on the size of the collector and interference with the electrical field. If the probes are too close together, there will be an interaction of the ground between the grounding probes, the fibers will be not pulled in different directions as desired in this inventive collector design. Each grounding probe needs to be electrically grounded independently from one another. In one embodiment, each grounding probe is connected to a grounding mesh (12), which is placed on the back of said collector body, and are electrically grounded independently from one another. The mesh may be made of any grounding materials that can evenly distribute an electrical ground including but not limiting to copper, silver or gold.

Figure 4:
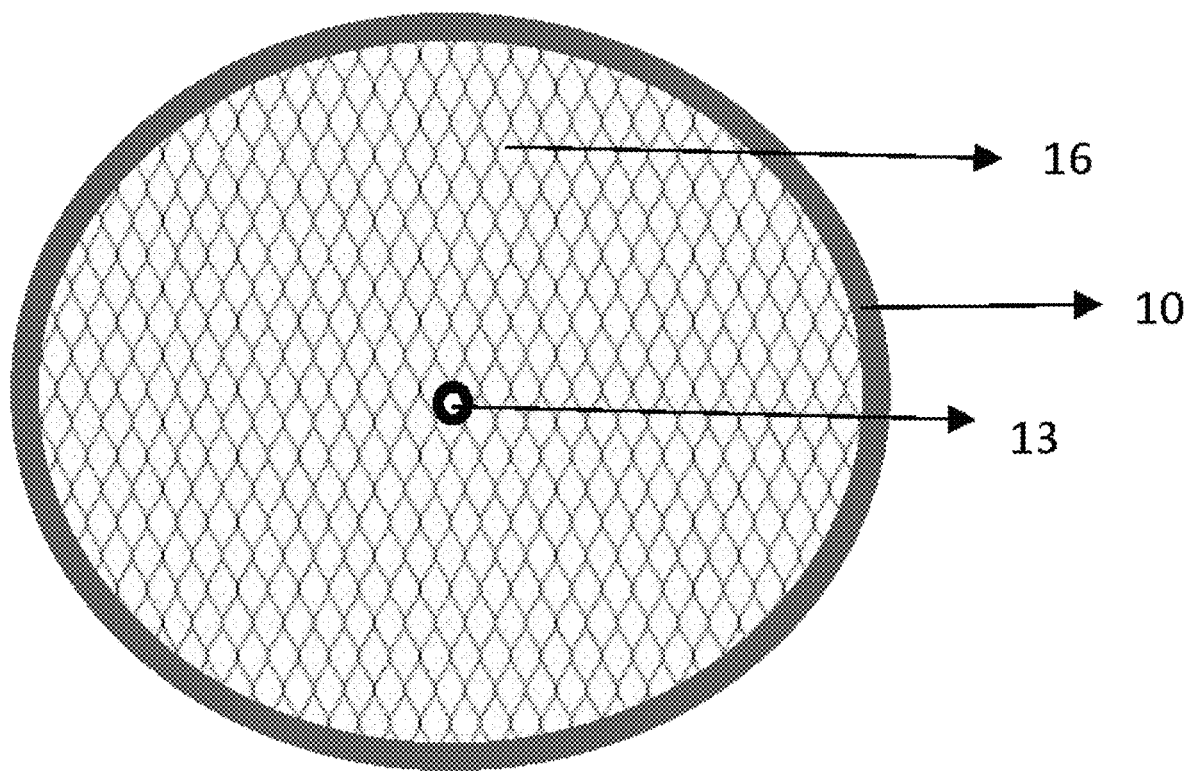
FIG. 4 shows top view a of the prototype mesh collector designed to ground the entire copper mesh grid to promote even distribution of fibers during the electrospinning process.

In still another embodiment, a three-dimensional electrospinning collector, comprising: a) a hollow The hollow collector body may be take many shape such as semi-sphere, semi-football, rectangular, or cube etc. semi-sphere non-conductive collector body; and a gridded mesh roughly cover the inside of said hollow semi-sphere non-conductive collector body; wherein the entire gridded mesh is electrically grounded (FIG. 4).

The hollow collector body may be take many shape such as semi-sphere, semi-football, rectangular, or cube etc., and may be made of any solid or semi solid electric non-conductive materials, including but not limited to Styrofoam, polycaprolactone (PCL), poly(l-lactic acid) (PLA), poly(l-lactic-co-glycolicacid) (PLGA), acrylonitrile butadiene styrene (ABS), and nylon. In a preferred embodiment, the collector body is hollow semi-sphere made of non-conductive material (10) Based on the materials used, the collector body may be form into the hollow semi-spherical shape using a variety of manufacturing techniques, including but not limiting to machine cutting, extrusion, 3D printing etc. The size of the collector is selected based on size of the 3D construct that it aimed to collect. The hollow semi-sphere non-conductive collector body may further include a means for attaching to a rotating mandrel. In one embodiment, the collector hold onto the mandrel via a hole (13) in center of the collector, which is slightly smaller than the mandrel. Other commonly used affixation methods may be used as long as it does not alter the electrical non-conducting property of the collector body. The gridded mesh (16) may be made of any grounding materials, including but not limiting to copper, aluminum, copper-clad aluminum, gold or silver. In one embodiment, a gridded mesh (16) covers the opening of the hollow semi-sphere non-conductive collector body, which faces the fiber source during electrospinning process. In another embodiment, the gridded mesh lines the inside surface of the hollow semi-sphere non-conductive collector body. Grid size will depend on the application of the 3D scaffold. Gauge size of the wire is dependent on the desired grid size.

III. Producing a 3D Scaffolding Construct Using the Inventive Collectors

FIG. 10 shows the basic set up of the an electrospinning apparatus using the inventive 3D collector. In a method of producing a three-dimensional scaffold by electrospinning, at least one fiber source (syringe pump) is loaded at a first potential with a solution formulation or melt. The inventive three-dimensional electrospinning collector (variable ground collector or mesh collector) is placed on a rotating mandrel adjacent to the fiber source at a second potential; and fiber from the fiber source is deposited into the inventive collets or generating a scaffold due to potential differences between the fiber source and the collector. In the embodiment, a variable ground collector is used, an electrical ground rotates around the back of the semi-sphere collector during electrospinning; process, makes contact with each grounding mash sequentially. As each mesh is electrically connected with a respective grounding probe, the fibers to be pulled in directions of each grounding probe different forming a desired pattern. In another embodiment, a mesh collector is used, fiber from the source forms small 3D scaffold between grid squares that leads to better porosity when compared to electrospinning done on a flat plate collector. Post processing technique, such as folding of the scaffolds may be used to create bigger 3D constructs. The fibers would collected both on the copper of the grid but also between the squares of the grief.

Example 1: Development of Prototype Electrospinning Collectors Capable of 3d Constructs for the Potential Use in Ridge Preservation Applications Collector Development
I. FLUF Collector (Prior Art Reported in Literature)

Figure 2:
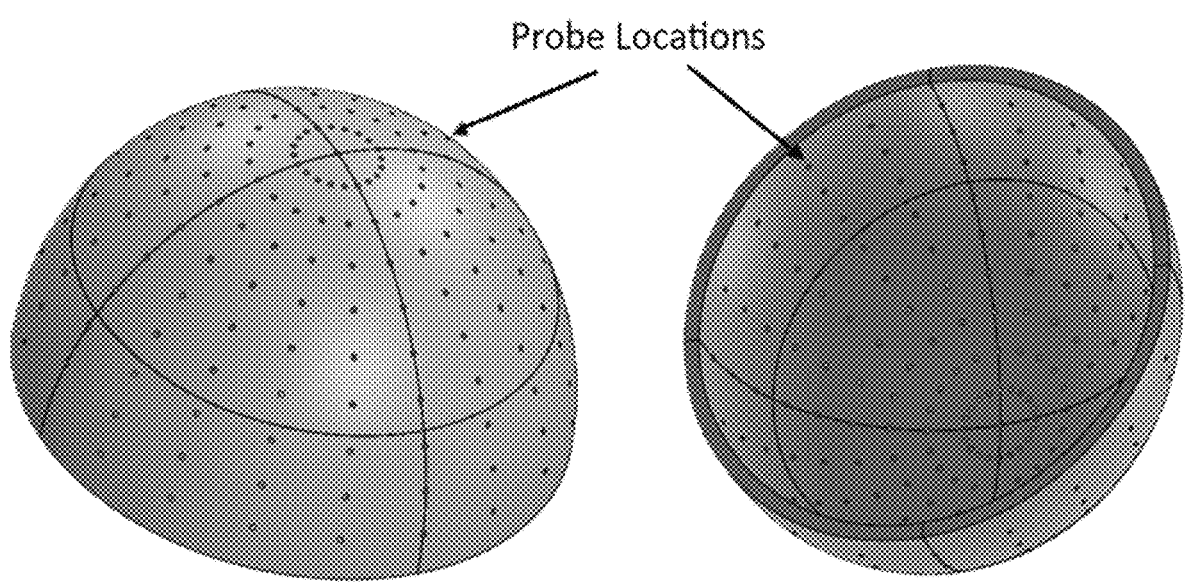
FIG. 2 shows a 3D printed half sphere collector mimicking what was seen in the literature (FLUF collector).

The FLUF collector was recreated according to the literature [18] by embedding 1.5-inch copper probes into a 3D printed half sphere 8-inches in diameter (FIG. 2). The probes were placed at 2-inch intervals from the center of the dish in 5 directions creating a symmetrical star pattern. The probes were collectively electrically grounded by attaching each of them to a single copper wire that was clipped to the ground.

II. Variable Ground Collector

A variable ground collector was fabricated using a Styrofoam half sphere (10) 8-inches in diameter by embedding rounded copper probes (11) (approximately halfway down the sphere in five equidistant directions (FIG. 3). Each copper probe is electrically grounded (12) independently from one another to provide a more guided electrospinning process into a star pattern as the collector spun on a mandrel during the electrospinning process.

III. Mesh Collector

The mesh collector was fabricated by lining a Styrofoam half sphere (10) 8-inches in diameter with a gridded copper mesh (16) (FIG. 4). The entire mesh was electrically grounded to promote fiber formation evenly along the interior surface of the half sphere.

Electrospun Scaffolds

Figure 5:
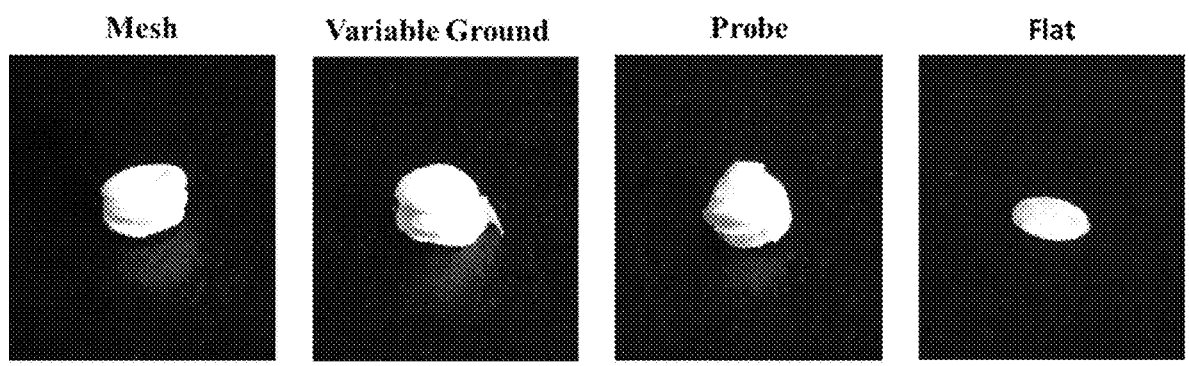
FIG. 5 shows pictures of the 4 mm biopsy punches cut of the folded scaffolds produced by each method.

Polycaprolactone was dissolved in hexafluoro-2-propanol (HFP) at 8% w/v and stirred at room temperature until the polymer was completely dissolved. The polymer solution was loaded into a 10 mL Luer lock syringe and fed through an 18-gauge line to the tip of an 18-gauge blunt tip needed. The syringe was loaded into a syringe pump and set to 2.0 mL/hr. The power supply was set to 10 kV and humidity was maintained between 16-26% during the electrospinning process. Collector types were placed 15 cm from the needle tip to the front plane of the collector. The same parameters were used for each collector type, and the resulting scaffolds were collected for comparisons to each other and to the flat plate spun scaffolds (FIG. 10). Post processing of each scaffold was carried out to maintain consistency between scaffolds during evaluations. In an effort to maintain the height consistency of each 3D scaffold, the electrospun sheets were lightly folded. Height of scaffolds are manipulated based on the number of folds performed. Additionally, to standardize the width, 4 mm biopsy punches were used to cut the folded scaffolds (FIG. 5).

Physical and Chemical Evaluations of 3-D Electrospun Scaffolds

Each scaffold was evaluated using laser microscopy (KEYENCE, Osaka, Japan) to determine pore size. The diameters of 5 randomly selected pores from three images of each collector were measured and averaged to determine pore size for that collector. Helium pycnometry (Micromeritics ACCUPYC™ 1340 gas pynometer, Norcross, GA) was used to determine porosity of the scaffolds. Chemical composition of the scaffolds were determined using Fourier transform infrared spectroscopy (FTIR) in transmission mode in the spectral range of 4000 to 650 $cm^{-1}$ with a resolution of 2 $cm^{-1}$, using a Spectrum 400 ATR-FTIR (PERKINELMER®, Waltham, MA). Three scans at random points on each material were taken and the resulting spectra averaged.

Biological Evaluations

Human osteosarcomas (Saos-2) were cultured at 37° C. with 5% CO2 in McCoy's 5A media and 15% fetal bovine serum. Media was changed every three days. After the cells reached confluence, cells were seeded (150,000 cells in 50 µL) onto 4 mm biopsy punches of each type of scaffolds for one hour. Cell attachment to the scaffolds was tested by rinsing the scaffolds in 1 mL of media after the one-hour attachment period and counting the cells. Approximately 45% of the cells seeded onto the scaffolds attached. Viability was monitored over 7 days with a Cell Counting Kit-8 (CCK-8) (Dojindo Molecular Technologies, Inc., Rockville, MD, USA) by placing 350 µL of the solution over each scaffold, incubating for 2 hours, collecting the solution, and running on a plate reader at 450 and 650 nm. Scaffolds were then washed with phosphate buffered saline (PBS) to remove dye remnants and replenished with media.

Statistical Analysis

Statistical analysis was carried out using analysis of variance (ANOVA) on Graphpad Prism (San Diego, CA, USA). Multiple comparisons were made among groups using Tukey's multiple comparison tests. Statistical significance was determined at p<0.05. Graphical representation was constructed using Graphpad Prism.

Results

I. Physical and Chemical Evaluations

Figure 6:
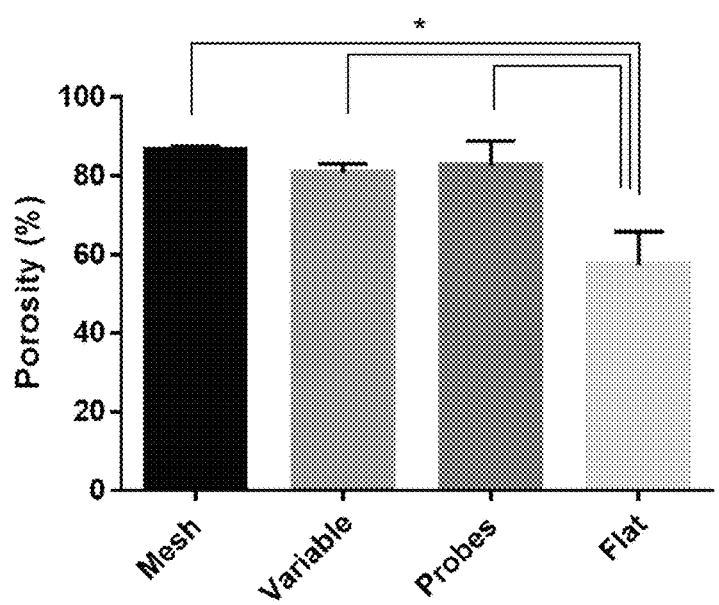
FIG. 6 is Helium pycnometry for porosity, which shows statistical significant ($p<0.05$) for scaffolds electrospun on 3D collectors vs. flat plate collector.

Scaffolds visualized with laser microscopy were shown to be more consistent and defect free from the mesh collector, possibly due to the more even distribution of the electrical ground. Scaffolds spun from the mesh collector (Table 1) also shows highest calculated pore size. Helium pycnometry results showed improved and statistically significant different porosity changes from all 3D collectors when compared to the flat plate collector (FIG. 6). However, the highest porosity was seen in the mesh collector spun scaffold, which may be because of the lighter, less dense areas that were observed between the grid's squares. Finally, FTIR showed no differences between any of the scaffolds (FIG. 7). FTIR results support that none of the electrospinning collectors has any effect on the chemical composition of the PCL.

TABLE 1

Calculated Pore Size of Scaffolds Produced from each Collector

| Collector type | Pore size (µm) |
| --- | --- |
| Probe | 6.3 |
| variable | 17.9 |
| Mesh | 20.9 |
| Flat | 15.8 |

II. Biological Evaluations

There were no statistically significant differences in the viability of cells seeded on all electrospun scaffolds including the flat plate collector (FIG. 8). Further, it shows that 3D constructs through electrospinning do not have a negative effect on cell viability.

Discussion

Collector Development
I. FLUF (Probe) Collector

In the literature, it is reported that scaffolds spun on the FLUF collector have a "cotton candy" like appearance and can be removed with a glass stir rod. In this study, that was not observed, and the reported scaffold could not be recreated. During the electrospinning process, observations showed excess collection of fibers at the tips of each copper probe, but there are hardly any fibers attached between the probes, which is what was expected in order to produce the cotton candy like appearance.

II. Variable Ground Collector

For variable ground collector, the probes were rounded as it was believed that the fibers were attracted to rough edges. This was shown to not be the case. Gross observation of fiber formation during the electrospinning process also showed an excess collection of fibers at the rounded probes. This collector was also designed to promote fiber formation between the probes instead of on the copper probes by producing a ground pull that alternated in a five-point star pattern instead of focusing on only one area. However, it is believed that the pull of the ground was not able to remain at one probe location long enough to manipulate the fibers in its direction before rotating to the next probe. To improve and potentially solve this issue, a rotating mandrel that is capable of rotating at a slower speed should be employed. Additionally, the prototype design may have had grounded electrical interference between probes, which may had an effect on fiber formation. An improved design of this collector will be considered in the future to improve the patterned pull of electrospun fibers to each grounded probe.

III. Mesh Collector

Gross observations of fiber formation during the electrospinning process showed a consistent distribution of fibers across the gridded copper mesh. This uniform patterning was confirmed with laser microscopy as the produced scaffolds showed much more consistency in the produced fibers (FIG. 9) when compared to the variable ground and probe collectors. Fibers collected along the grid of the mesh were denser than in between each square of copper mesh where fibers were lighter and more "airy." This is likely due to a more uniform distribution of charges along the copper grid of the mesh that attracted more fibers to their location. However, due to the close proximity of each gridded square, fibers were still able to form between them. Scaffolds spun onto the copper mesh were also much easier to collect when compared to the other collectors.

Conclusion

The current study demonstrated a simple and reproducible method of electrospinning with collectors that produce 3D scaffolds, which showed significant improvement in their porosity and pore size when compared to flat plate collector spun scaffolds, without affecting biocompatibility. Porosity and pore size results, as well as observed ease of production, demonstrated that the mesh collector produced the most optimal PCL scaffolds. However, it can also be concluded that any 3D electrospun construct produced with PCL, given the porosity and pore size reported here, should have the same biological compatibility. Due to the biocompatibility of PCL [20], the 3D constructs produced herein have the required architecture and potential to be used in biomedical applications that require volumetric support.

Example 2: Development and Characterization of a Collagen Attached and Mineralized 3D Electrospun Scaffolds for its Potential Use in Alveolar Ridge Preservation The periodontium, which includes gingiva, connective tissue, cementum, periodontal ligament, and alveolar bone, surround and anchor a tooth in the maxillary or mandibular alveolar process [21]. The alveolar bone consists of three components: cortical bone, cancellous trabeculae and alveolar bone proper, composing the tooth socket. Following a tooth extraction, the alveolar bone undergoes remodeling, especially after a difficult extraction, with additional bone loss due to surgical trauma. In most cases, implant therapy is considered post-extraction to restore form, function, and esthetics. Reconstruction and implantation success is dependent on sufficient alveolar bone volume and favorable ridge architecture [21, 22]. One major limitation in dental implant placement is the presence of insufficient bone to support osseointegration. Failure in maintaining the residual bony ridge after tooth extraction, may necessitate extensive, unpredictable surgical augmentation of the ridge.

Clinically, the use of materials and biomaterials for grafting has received considerable attention. Grafts are generally classified per their source: autografts, allograft, xenograft and alloplasts. Although multiple studies have consistently shown that treatment with grafting material decreases the level of ridge resorption, no conclusive evidence currently exists to suggest that one type of grafting material performs significantly better than any others [22, 23]. The application of the graft material to the socket can vary considerably between clinicians. Additionally, many of the available graft materials are in a lyophilized powder form that is difficult to pack and maintain in the tooth socket [24, 25]. As such, development of an osteoconductive and easy-to-use scaffolding material would provide a valuable product by promoting guided bone regeneration and ridge preservation for implant therapy.

Traditional electrospinning produces a flat, compressed, interconnected scaffold consisting of tightly packed nanofibers. These nanofiber scaffolds have been shown to have large specific surface area for the incorporation and delivery of bioactive molecules and/or drugs as well as the capability to support the adhesion, growth, and function of various cell types. In addition, the morphology of the scaffolds is highly tunable by the modification of fabrication parameters, such as polymer concentration, applied voltage, or the spinneret-collector distance. As such, the adaptability of electrospinning makes it advantageous in the development of novel scaffolds for tissue engineering and drug delivery systems. A major limitation of traditional electrospun scaffolds is densely packed fiber layers, the lack of space between the layers creates 2D sheets with superficial planar pores (0.35 to 1 μm). This compact sheet structure limits cell infiltration and growth throughout the scaffold. There is a need for the development of a fabrication methodology that can produce stable 3D structures, while exhibiting nano-scale morphology and interconnected porosity, which is more biomimetic. Ideally, placement of a mineralized FLUF-fabricated collagen scaffold at the time of extraction will prevent this complication. However, current approaches to ridge preservation can be technique sensitive and expensive. An alternative material providing user friendly handling properties at a lower cost is highly desirable [22, 23].

The present invention is directed to a method using previously discussed 3D collector to produce a three-dimensional (3D) electrospun collagen attached and mineralized nanofibrous scaffold for its potential use in alveolar ridge preservation. The new 3-d material aim to promote an improved rate of bone-fill at the extraction site, with the purpose of decreasing the time between extraction and implant placement.

To functionalize the surface of the 3D PCL scaffolds, reactive free amine groups was introduced to the surface, using 1, 6-hexanediamene. Subsequently, a bioactive layer of collagen was covalently attached to the PCL through the use of glutaraldehyde (GA) and also 1-ethyl-3-(3-dimethyl-amino-propyl) carbodiimide hydrochloride (EDC) coupled with N-hydroxysulfosuccinimide (sulfo-NHS). Finally, nano-sized hydroxyapatite (HA) was precipitated onto the collagen-based nanofibrous scaffold using a passive and biomimetic method mimicking physiological simulated body fluid (SBF). Results from FTIR indicate the GA method of collagen attachment coupled with mineralization for 7 days gave the strongest signal of collagen and HA. Biological performance determined the scaffolds biocompatible with no statistically significant differences seen between scaffolds mineralized for less time. The study herein has demonstrated a successful method of producing 3D electrospun and functionalized constructs for their potential use in alveolar ridge preservation.

Development of Collagen Attached and Mineralized 3D Electrospun Scaffolds

I. Electrospinning

Electrospinning parameters were as previously described, and scaffolds were collected using the gridded copper mesh collector. PCL was dissolved in hexafluoro-2-propanol (HFP) at 8% w/v and stirred at room temperature until the polymer was completely dissolved. The polymer solution was loaded into a 10 mL luer-lock syringe and fed through an 18-gauge line to the tip of an 18-gauge blunt tip needle. The syringe was loaded into a syringe pump and set to 2.0 mL/hr. The power supply was set to 10 kV and humidity was maintained between 16-26% during the electrospinning process. The collector was placed 15 cm from the needle tip to the front plane of the collector and the electrospinning process was carried out until an even distribution of fibers had been spun across the entire grid. The scaffold was collected, and a 4 mm biopsy punch was used to collect multiple samples from the same electrospun scaffold.

II. Viscosity and Conductivity

Viscosity and conductivity of the 8% w/v PCL solution was taken for reference. Viscosity was taken using a viscometer (Brookefield CAP1000 Viscometer, AMETEK Brookefield, Middleborough, MA) by placing 300 μL of the polymer solution on the testing platform, setting the speed to 750 rpm, and letting each test run for the recommended time of 15 seconds using spindle 1 provided with the viscometer. The polymer was tested 5 different times and the results were averaged. Conductivity was taken using a particle size analyzer (Malvern Zetasizer, Malvern, UK). Approximately 1 mL of the polymer solution was placed in a disposable capillary cell and run 3 times with 12 scans for each run. The resulting values were averaged.

III. Aminolysis

Scaffolds that had been cut into 4 mm biopsy punches were used for this experiment. A method previously reported [6] on for the optimization of aminolyzing PCL scaffolds was utilized by preparing a 10% w/v solution of hexamethylenediamine (HMDA) dissolved in 2-propanol. Scaffolds were placed in a non-treated 96-well plate and 200 μL of HMDA solution was added to each well. Scaffolds were allowed to incubate at 37° C. for 1 hour. Then, each scaffold was individually placed in 100 mL of distilled water and washed on a shaker at room temperature for 24 hours. Finally, scaffolds were removed from the water wash and dried for 24 hours in a vacuum desiccator.

IV. Collagen Attachment

Two methods of collagen attachment were explored including a glutaraldehyde (GA) method and 1-Ethyl-3-(3-dimethylaminopropyl)carbodiimide/N-hydroxysuccinimide (EDC/NHS) crosslinking method.

V. Glutaraldehyde (GA) Method

This method was accomplished following the literature [6] by preparing a 1 wt % glutaraldehyde solution and immersing each aminolyzed scaffold in 200 µL of the GA solution. Scaffolds were removed from the solution and individually placed in 100 mL of distilled water and washed on a shaker for 24 hours. Once removed from the water wash scaffolds were immersed in a 6 mg/mL collagen solution (Sigma) that had been previously diluted and pH adjusted to 3.4 for 24 hours at 2-4° C. Once removed from the collagen solution, scaffolds were dunked 3 times in a 1% acetic acid solution to removed excess collagen that did not chemically attach. Finally, scaffolds were rinsed individually in 100 mL of distilled water for 24 hours at 2-4° C. and then dried inside a desiccant chamber for 24 hours at 2-4° C.

VI. EDC/NHS Method

Three techniques of utilizing the EDC/NHS method of collagen attachment were explored. In all three techniques, a 0.5 M solution of EDC and NHS were prepared separately in MES buffer and a 6 mg/mL bovine collagen solution (Millipore Sigma, 804622, Burlington, MA). was used as purchased. Additionally, 250 µL EDC, 250 µL NHS, and 500 µL collagen solution was used for every technique per each 4 mm biopsy punched scaffold and each scaffold was soaked in MES buffer for 15 minutes prior to experiments.

In the first method technique, the collagen solution was added to the EDC/NHS solution and allowed to react for 15 minutes, following the scaffold was placed in the solution for 1 hour. In the second method, the PCL scaffold was added to the EDC/NHS solution and allowed to react for 15 minutes and then collagen was added for 1 hour. The third method involved the addition of all three components; EDC/NHS, collagen solution, and PCL scaffold all at once for 1 hour. These techniques were chosen to manipulate the chemistry of the reaction by 1) promoting crosslinking of the EDC/NHS solution to collagen first, 2) promoting crosslinking of EDC/NHS to the PCL scaffold first, and 3) promoting the crosslinking of collagen to the scaffold as well as to itself all at once time.

VII. Passive Mineralization in Simulated Body Fluid (SBF)

Simulated body fluid was prepared according to the literature [27] by dissolving the constituents in the order they are listed, seen in table 1. Because of the supersaturation of apatite in the fluid, precipitation can happen without careful preparation. The solution was kept at 36.5° C. throughout the preparation process, plastic beakers were used to prevent precipitation onto glass, and if the solution became cloudy at any point during preparation (indicating precipitation), the experiment was abandoned and began again.

Once preparation of SBF was complete, aminolyzed, collagen attached scaffolds were soaked in 50 mL of SBF for 1, 5, and 7 days at 37° C. At the end of each time point, scaffolds were collected and placed in a desiccant chamber to dry and stored at 2-4° C. for further testing.

Physical and Chemical Evaluations

Laser microscopy (Keyence) was utilized to observe the morphological changes in the altered scaffolds. Post processing of Keyence images was performed with ImageJ (NIH) to determine pore size by taking the diameter of 5 different pores from 3 different images of each scaffold. Helium pycnometry (Micromeritics ACCYPYC™ 1340 gas pycnometer, Norcross, GA) was used to determine porosity. Fourier transform infrared spectroscopy (FTIR) in transmission mode in the spectral range of 4000 to 6500 $cm^{-1}$ with a resolution of 2 $cm^{-1}$, using a Spectrum 400 ATR-FTIR (PERKINELMER®, Waltham, MA) was taken to observe chemical composition changes. Three scans at random points on each material was taken and the spectra were averaged.

Biological Evaluations

To determine mineralization time that showed optimal cellular response, human osteoblasts (HOB) (PromoCell, Heidelberg, Germany) were cultured at 37° C. with 5% CO2 in osteoblast growth medium per manufacturer's instructions. Media was changed every 3 days. After the cells reached confluence, cells were seeded (150,000 cells in 50 µL) onto 4 mm biopsy punches of pure PCL (control), PCL mineralized for 1, 5, and 7 days, and J-Bone (positive control). Viability was monitored over 3 days with Cell Counting Kit-8 (CCK-8) (Dojindo Molecular Technologies, Inc., Rockville, MD) by placing 350 µL of the solution over each scaffold, incubating for 2 hours, collecting the solution, and running on a plate reader, in duplicate, at 450 and 650 nm. Scaffolds were then washed with phosphate buffered saline (PBS) to remove dye remnants and replenished with media to reuse for the next time point collection.

Data Analysis

Fabricated scaffolds using the same methodology were compared within the group by an independent Student's t-test for groups of data or one-way analysis of variance (ANOVA) for multiple sets of data using GraphPad Prism. A confidence level of 95% ($p<0.05$) was considered to be statistically significant.

Results and Discussion

I. Viscosity and Conductivity

Viscosity and conductivity can result in high differences in morphological change of fibers and can be manipulated with a change in concentration of the polymer solution and the addition of salt, respectively [28-30]. While this study

TABLE 2

Reagents required to prepare 1000 mL of SBF [27]

| Order | Reagent | Amount | Container | Purity (%) | Formula weight |
|---|---|---|---|---|---|
| 1 | NaCl | 8.035 g | Weighing paper | 99.5 | 58.4430 |
| 2 | $NaHCO_3$ | 0.355 g | Weighing paper | 99.5 | 84.0068 |
| 3 | KCl | 0.225 g | Weighing bottle | 99.5 | 74.5515 |
| 4 | $K_2HPO_4 \cdot 3H_2O$ | 0.231 g | Weighing bottle | 99.0 | 228.2220 |
| 5 | $MgCl_2 \cdot 6H_2O$ | 0.311 g | Weighing bottle | 98.0 | 203.3034 |
| 6 | 1.0 m-HCl | 39 ml | Graduated cylinder | — | — |
| 7 | $CaCl_2$ | 0.292 g | Weighing bottle | 95.0 | 110.9848 |
| 8 | $Na_2SO_4$ | 0.072 g | Weighing bottle | 99.0 | 142.0428 |
| 9 | Tris | 6.118 g | Weighing paper | 99.0 | 121.1356 |
| 10 | 1.0 m-HCl | 0-5 ml | Syringe | — | — | did not manipulate viscosity or conductivity to observe fiber morphology changes, the polymer concentration chosen consistently produced defect free, continuous fibers. Viscosity and conductivity for the 8% w/v PCL solution are reported for reference in table 3.

TABLE 3

Viscosity and Conductivity of 8% w/v PCL solution

| Viscosity | 69.2 cP |
|---|---|
| Conductivity | 2.8 µS/cm |

Physical Characterization and Porosity

Gross observations of scaffolds mineralized in SBF for 1, 5, and 7 days show mineral production increase over the 7-day study (FIG. 11). Porosity evaluations using helium pycnometry and laser microscopy produced two distinctly different results. Helium pycnometry shows a statistically higher porosity percentage across all scaffolds when compared to laser microscopy (Table 4).

The wide range of results are likely due to the surface modification step of scaffold fabrication. When the scaffolds are soaked in SBF and mineralized, the mineralization likely only occurred on the surface level of each scaffold as the passive process was used. Because of this, HA attached to the surface fibers of the scaffold, decreasing the surface porosity but not the overall porosity of the scaffold. Laser microscopy was more sensitive to the mineralization as it is only able to penetrate a few layers into the scaffold while helium pycnometry is able to penetrate the entire depth of the scaffold thus not affecting its porosity results. Additionally, as seen using both techniques, the increased time in SBF resulted in more mineralization and had an overall decrease on the porosity of the scaffolds. Pore size correlated with porosity data. As mineralization time increased, pore size decreased. Control scaffolds soaked in SBF for the same amount of time also show a decrease in pore size, which is likely due to swelling of the fibers rather than mineralization as no mineral content was observed on the surface of control scaffolds. While these results show sub-optimal pore size necessary for immediate cellular infiltration, the scaffolds should not be disregarded for their potential in ridge preservation therapy as these results are consistent with electrospinning expectation. However, further studies could investigate the ability to increase pore size of the scaffolds while maintaining high porosity.

TABLE 4

Porosity and pore size evaluations of scaffolds using helium pycnometry and laser microscopy

| | Helium Pycnometry Porosity (%) | Keyence Laser Microscopy Porosity (%) | Pore Size (µm) |
|---|---|---|---|
| Collagen Attached | 72.6% | 37.5% | 16.4 |
| Mineralized 5 Days | 60.2% | 31.7% | 14.9 |
| Mineralized 7 Days | 62.1% | 19.9% | 11.86 |
| PCL Control in SBF for 5 Days | 71.0% | 38.9% | 13.8 |
| PCL Control in SBF for 7 Days | 72.8% | 29.5% | 13.4 |

Molecular and Chemical Composition

Fourier-transform infrared spectroscopy (FTIR) results show that the strongest signal of collagen was on scaffolds that were collagen attached using the GA technique (FIG. 12). Since this technique produced the strongest collagen signal, scaffolds produced using this technique were chosen to mineralize. FTIR results of mineralized scaffolds show the largest signal of HA in the scaffolds mineralized for 7 days (FIG. 13). However, it was observed that the more mineralized scaffolds dampen the signal of the attached collagen. This is likely due to how the HA mineralized onto the scaffolds. HA is attracted to the collagen on the surface of the scaffolds and deposits more efficiently along the collagen attached fibers than it does pure PCL fibers.

In Vitro Cell Viability of Human Osteoblasts

CCK8 results showed attachment and viability on all scaffold types including plain PCL and a J-Bone block positive control for up to 72 hours (FIG. 14). Results show that osteoblasts prefer the bone control over the synthetic PCL that had been functionalized with collagen and mineralized. This is to be expected as autogenous bone is the gold standard for alveolar ridge preservation therapy, however, not always available or possible hence the need for an alternative. Results also show no statistically significant difference in collagen attached scaffolds mineralized for 1, 5, or 7 days. This is of particular interest because it was previously hypothesized that mineralization could have an effect on osteoblast function, however no effects on viability was observed. A future study with scaffolds mineralized from all time points will be performed to look at the effect that different degrees of mineralization may have on osteoblast production of osteocalcin, osteonectin, and osteopontin.

CONCLUSION

The current study demonstrates a methodology capable of producing a collagen attached and mineralized scaffold for potential use in alveolar ridge preservation that shows improved porosity and pore size in support of cellular viability. Future studies will look at how the scaffolds effect production of different osteoblast produced biomarkers before a potential in vivo study of the product is explored. Additionally, studies will be done to observe cellular infiltration into the scaffolds as well as release kinetics on the attached collagen. The architecture of the 3D scaffold offers a platform for various surface modification capabilities that can be tuned based on different biomedical applications other than alveolar ridge preservation, however, other cell types should also be tested with the produced scaffolds.

REFERENCES

1. Angammana, C. J. and S. H. Jayaram. *A theoretical understanding of the physical mechanisms of electrospinning.* in *Proc. ESA Annual Meeting on Electrostatics.* 2011.
2. Kai, D., S. S. Liow, and X. J. Loh, *Biodegradable polymers for electrospinning: towards biomedical applications.* Materials Science and Engineering: C, 2014. 45: p. 659-670.
3. Hohman, M. M., et al., *Electrospinning and electrically forced jets. I. Stability theory.* Physics of fluids, 2001. 13(8): p. 2201-2220.
4. Vaseashta, A., *Controlled formation of multiple Taylor cones in electrospinning process.* Applied Physics Letters, 2007. 90(9): p. 093115.
5. Kong, C. S., et al., *Electrospinning mechanism for producing nanoscale polymer fibers.* Journal of Macromolecular Science®, Part B: Physics, 2010. 49(1): p. 122-131.

6. Doshi, J. and D. H. Reneker. *Electrospinning process and applications of electrospun fibers.* in *Conference Record of the 1993 IEEE Industry Applications Conference Twenty-Eighth IAS Annual Meeting.* 1993. IEEE.
7. Deitzel, J. M., et al., *Controlled deposition of electrospun poly (ethylene oxide) fibers.* Polymer, 2001. 42(19): p. 8163-8170.
8. Shabani, I., et al., *Cellular infiltration on nanofibrous scaffolds using a modified electrospinning technique.* Biochemical and biophysical research communications, 2012. 423(1): p. 50-54.
9. Ghasemi-Mobarakeh, L., et al., *The thickness of electrospun poly (ε-caprolactone) nanofibrous scaffolds influences cell proliferation.* The International journal of artificial organs, 2009. 32(3): p. 150-158.
10. Lowery, J. L., N. Datta, and G. C. Rutledge, *Effect of fiber diameter, pore size and seeding method on growth of human dermal fibroblasts in electrospun poly (ε-caprolactone) fibrous mats.* Biomaterials, 2010. 31(3): p. 491-504.
11. Haider, A., S. Haider, and I.-K. Kang, *A comprehensive review summarizing the effect of electrospinning parameters and potential applications of nanofibers in biomedical and biotechnology.* Arabian Journal of Chemistry, 2018. 11(8): p. 1165-1188.
12. Rnjak-Kovacina, J. and A. S. Weiss, *Increasing the pore size of electrospun scaffolds.* Tissue Engineering Part B: Reviews, 2011. 17(5): p. 365-372.
13. Nam, J., et al., *Improved cellular infiltration in electrospun fiber via engineered porosity.* Tissue engineering, 2007. 13(9): p. 2249-2257.
14. Ji, C., et al., *Fabrication of poly-DL-lactide/polyethylene glycol scaffolds using the gas foaming technique.* Acta biomaterialia, 2012. 8(2): p. 570-578.
15. Jun, I., et al., *Electrospun fibrous scaffolds for tissue engineering: Viewpoints on architecture and fabrication.* International journal of molecular sciences, 2018. 19(3): p. 745.
16. Bulysheva, A. A., et al., *Low-temperature electrospun silk scaffold for in vitro mucosal modeling.* Journal of Biomedical Materials Research Part A, 2012. 100(3): p. 757-767.
17. Yang, X., J. D. Shah, and H. Wang, *Nanofiber enabled layer-by-layer approach toward three-dimensional tissue formation.* Tissue Engineering Part A, 2009. 15(4): p. 945-956.
18. Blakeney, B. A., et al., *Cell infiltration and growth in a low density, uncompressed three-dimensional electrospun nanofibrous scaffold.* Biomaterials, 2011. 32(6): p. 1583-1590.
19. Kim, M. S., et al., *Highly porous 3D nanofibrous scaffolds processed with an electrospinning/laser process.* Current Applied Physics, 2014. 14(1): p. 1-7.
20. Mondal, D., M. Griffith, and S. S. Venkatraman, *Polycaprolactone-based biomaterials for tissue engineering and drug delivery: Current scenario and challenges.* International Journal of Polymeric Materials and Polymeric Biomaterials, 2016. 65(5): p. 255-265.
21. Tomlin, E. M., S. J. Nelson, and J. A. Rossmann, *Ridge preservation for implant therapy: a review of the literature.* The open dentistry journal, 2014. 8(1).
22. Barone, A., et al., *Xenograft versus extraction alone for ridge preservation after tooth removal: a clinical and histomorphometric study.* Journal of periodontology, 2008. 79(8): p. 1370-1377.
23. Horowitz, R., D. Holtzclaw, and P. S. Rosen, *A review on alveolar ridge preservation following tooth extraction.* Journal of Evidence Based Dental Practice, 2012. 12(3): p. 149-160.
24. Scabbia, A. and L. Trombelli, *A comparative study on the use of a HA/collagen/chondroitin sulphate biomaterial (Biostite®) and a bovine-derived HA xenograft (Bio-Oss®) in the treatment of deep intra-osseous defects.* Journal of clinical periodontology, 2004. 31(5): p. 348-355.
25. Marinucci, L., et al., *Effects of hydroxyapatite and Biostite® on osteogenic induction of hMSC.* Annals of biomedical engineering, 2010. 38(3): p. 640-648.
26. Zhu, Y., et al., *Surface modification of polycaprolactone membrane via aminolysis and biomacromolecule immobilization for promoting cytocompatibility of human endothelial cells.* Biomacromolecules, 2002. 3(6): p. 1312-1319.
27. Kokubo, T. and H. Takadama, *How useful is SBF in predicting in vivo bone bioactivity?* Biomaterials, 2006. 27(15): p. 2907-2915.
28. Angammana, C. J. and S. H. Jayaram. *A theoretical understanding of the physical mechanisms of electrospinning.* in *Proc. ESA Annual Meeting on Electrostatics.* 2011.
29. Drew, C., et al., *The effect of viscosity and filler on electrospun fiber morphology.* Journal of Macromolecular Science, Part A, 2003. 40(12): p. 1415-1422.
30. Nezarati, R. M., M. B. Eifert, and E. Cosgriff-Hernandez, *Effects of humidity and solution viscosity on electrospun fiber morphology.* Tissue Engineering Part C: Methods, 2013. 19(10): p. 810-819.
31 Yang Y., Jia Z., Liu J., Li Q., Hou L., Wang L., and Guan Z. *Effect of electric field distribution uniformity on electrospinning.* Journal of Applied Physics 103, 104307 (2008).

What is claimed is:

1. An three-dimensional electrospinning collector, comprising:
    a) a hollow semi-sphere non-conductive collector body; and
    b) a plurality of grounding probes are embedded inside the collector body approximately halfway down the sphere in equidistant directions;
    wherein each grounding probe is electrically grounded independently from one another.

2. The three-dimensional electrospinning collector of claim 1, wherein said hollow semi-sphere non-conductive collector body is made of cell extruded polystyrene foam (XPS), polycaprolactone (PCL), poly (l-lactic acid) (PLA), poly (l-lactic-co-glycolicacid) (PLGA), acrylonitrile butadiene styrene (ABS), or nylon.

3. The three-dimensional electrospinning collector of claim 1, wherein each said grounding probe is electrically connected to a grounding mesh placed on the back of said collector body, which are electrically grounded independently from one another.

4. The three-dimensional electrospinning collector of claim 3, wherein said grounding probe and grounding mesh is made of electrical grounding material.

5. The three-dimensional electrospinning collector of claim 4, where the grounding probe and grounding mesh is made of copper, aluminum, copper-clad aluminum, gold or silver.

6. A three-dimensional electrospinning collector, comprising:
   a) a hollow semi-sphere non-conductive collector body; and
   b) a gridded mesh covers inside of said hollow semi-sphere non-conductive collector body;
   wherein the gridded mesh is electrically grounded.

7. The three-dimensional electrospinning collector of claim 6, wherein said hollow semi-sphere non-conductive collector body is made of cell extruded polystyrene foam (XPS), polycaprolactone (PCL), poly (l-lactic acid) (PLA), poly (l-lactic-co-glycolicacid) (PLGA), acrylonitrile butadiene styrene (ABS), or nylon.

8. The three-dimensional electrospinning collector of claim 6, wherein said gridded mesh is made of copper, aluminum, copper-clad aluminum, gold or silver.

9. The three-dimensional electrospinning collector of claim 6, wherein said gridded mesh covers an opening of said hollow semi-sphere non-conductive collector body.

10. The three-dimensional electrospinning collector of claim 6, wherein said gridded mesh lines an inside surface of said hollow semi-sphere non-conductive collector body.

\* \* \* \* \*